United States Patent
Liu et al.

(10) Patent No.: US 10,670,609 B2
(45) Date of Patent: Jun. 2, 2020

(54) YTTERBIUM AS A SURROGATE CATION TO MEASURE CALCIUM FLUX

(71) Applicant: Government of the United States, as represented by the Secretary of the Air Force, Wright-Patterson AFB, OH (US)

(72) Inventors: Jingbo Liu, Corpus Christi, TX (US); Sajid Bashir, Corpus Christi, TX (US); Jeffrey C. Wigle, Universal City, TX (US)

(*) Notice: Subject to any disclaimer, the term of this patent is extended or adjusted under 35 U.S.C. 154(b) by 313 days.

(21) Appl. No.: 15/712,628

(22) Filed: Sep. 22, 2017

(65) Prior Publication Data

US 2019/0094241 A1 Mar. 28, 2019

(51) Int. Cl.
*G01N 33/68* (2006.01)
*G01N 33/84* (2006.01)

(52) U.S. Cl.
CPC ....... *G01N 33/6872* (2013.01); *G01N 33/84* (2013.01)

(58) Field of Classification Search
None
See application file for complete search history.

(56) References Cited

U.S. PATENT DOCUMENTS

| | | | |
|---|---|---|---|
| 8,546,403 B2 | 10/2013 | Whitten | |
| 9,079,891 B2 | 7/2015 | Whitten | |
| 2004/0121445 A1* | 6/2004 | Marino | C12N 1/20 435/252.3 |
| 2006/0014938 A1* | 1/2006 | Groman | A61K 41/009 534/15 |
| 2015/0045664 A1* | 2/2015 | Saha | A61K 49/0004 600/431 |
| 2015/0322012 A1 | 11/2015 | Whitten | |

OTHER PUBLICATIONS

Dai et al. J of Rare Earth Metals vol. 33(4) p. 445 (Year: 2015).*
Jeffry B. Lansman, "Blockade of current through single calcium channels by trivalent lanthanide vations," J. Gen. Physiol., vol. 95 (1990) 679-696.
J. C. Wigle, "Nitric oxide measurements in hTERT-RPE cells and subcellular fractions exposed to low levels of red light," Mech. Low Light Thermapy IX, Proc. SPIE, vol. 8932:89320D (2014) San Francisco, CA.
R. W. Williams et al, "Protein secondary structure analysis using Raman amide I and amide III spectra," Methods Enzymol., vol. 130 (1986) 311-331.
H. R. Morris et al., "Imaging spectrometers for fluorescence and Raman microscopy: acousto-optic and liquid crystal tunable filters," Appl. Spectroscopy, vol. 48 (1994) 857-866.
Freudiger et al., "Label-free biomedical imaging with high sensitivity by stimulated Raman scattering microscopy," Science, vol. 322 (2008) 1857-1861.
A. Zumbusch et al., "Three-dimensional vibrational imaging by coherent Anti-Stokes Raman scattering," Phys. Rev. Lett., vol. 82 (1999) 4142-4145.
K. C. Schuster et al., "Single-cell analysis of bacteria by Raman microscopy: spectral information on the chemical composition of cells and on the heterogeneity in a culture," J. Microbiol., Methods, vol. 42 (2000) 29-38.

* cited by examiner

*Primary Examiner* — Blaine Lankford
(74) *Attorney, Agent, or Firm* — AFMCLO/JAZ

(57) ABSTRACT

A method for tracking calcium flux of a eukaryotic cell. The method includes growing the eukaryotic cell in the presences of a ytterbium salt in solution and spectroscopically measuring ytterbium in the eukaryotic cell.

17 Claims, 6 Drawing Sheets

YTTERBIUM AS A SURROGATE CATION TO MEASURE CALCIUM FLUX

RIGHTS OF THE GOVERNMENT

The invention described herein may be manufactured, used, and licensed by or for the Government of the United States for all governmental purposes without the payment of any royalty.

FIELD OF THE INVENTION

This invention relates to the field of cellular biology. More particularly, this invention relates to tracking of certain physiological processes within a eukaryotic cell.

BACKGROUND OF THE INVENTION

Divalent calcium cation ($Ca^{2+}$, but referred to herein as calcium or calcium ion or cation) is present in all eukaryotic cells 12 and performs many physiological functions, such as metabolic signaling and cellular homeostasis. FIG. 1 illustrates movement, or flux, of calcium, through the cellular membrane 10 in and out of the cell 12 or between the cytoplasm 14 and subcellular organelles, such as mitochondria 16 and endoplasmic reticulum 18, in response to physiological signals by way of one or more types of calcium channels or pumps 20, 22, 24. These ion movements temporarily create localized potential gradients, or capacitances, which are used by the cell 12 in chemical communication.

Cellular transduction involving calcium-based signaling is ubiquitous within biological organisms utilizing aerobic respiration. The release of calcium ions from organelles into the cytoplasm 14 triggers other "response factors," such as nitric oxide ("NO") production. NO production has a number of divergent roles, including radical species quencher. The production of NO, therefore, aids the cell 12 in withstanding oxidative stress, instead of undergoing cell death.

More particularly, irradiation of the eukaryotic cell 12 may cause inhibition of adenylate cyclase and reduction of cyclic adenosine monophosphate ("cAMP"), which results in the inhibition of protein kinase A ("PKA") and cAMP response element binding protein/activation transcription factor ("TF") in the nucleus 26. Meanwhile, nuclear factors activate phospholipase C pathways. The consequent increase in calcium concentration phosphorylates protein kinase C ("PKC"), which activates nuclear responsive factors that ultimately activate PKC. PKC activation may also activate NF-kappa B ("NFκB") and other TFs. A small increase in calcium induces NO biosynthesis, which via a feedback loop, decreases calcium concentration and inhibits PKC.

Other regulatory proteins activated by calcium-mediated proteins activate several mitogen-activated protein kinases. For example, extracellular regulated kinase ("ERK") and Jun N-terminal kinase ("JNK"), which regulate immunoglobulin E ("IEG") activation and gene transcription.

High levels of NO inhibit calcium/calmodulin complex ("Ca-CaM") by direct binding. Lowered calcium concentrations mediated by melatonin receptors (MT1/2) are reported in the literature and would inhibit calmodulin kinase ("CaMK"), which in turn regulates NFκB, the retinoid-related receptor, and other TF activation. CaMK may also regulate PKC.

As was briefly noted above, NO assists in free radical quenching. Changes in cellular redox states toward more reduced environments produce protein reduction that may lead to enzyme activation. The environment may also induce translational changes, which may increase enzyme concentrations. Finally, a decrease in free radicals would allow repression of redox-sensitive TFs (for example, NFκB), which would regulate gene transcription.

Calcium is ubiquitous in eukaryotic cells, as alluded to above. Yet, the movement of calcium (intra- and extracellularly) has been conventionally difficult to observe in real time without using a marker. There are a number of commercially-available, calcium-sensitive fluorescent dyes configured to bind to calcium in the cytoplasm. Upon calcium binding, these commercially-available probes can be stimulated to emit light in the form of fluorescence, which can be measured easily using conventional methods.

Other commercially-available calcium indicators do not rely on fluorescence. For example, 1,2-Bis(2-amino-phenoxy)ethane-N,N,N',N'-tetraacetic acid tetrakis (acetoxymethyl ester) [BAPTA AM] is a non-fluorescent, calcium chelator configured to selectively bind calcium. However, there are some problems with BAPTA AM. For example, BAPTA AM cannot penetrate into subcellular organelles 16, 18 from the cytoplasm 14. BAPTA AM (and other similar chelators) are limited by sensitivity (for example, a minimum calcium concentration may be necessary before binding occurs) and selectivity (for example, binding of $Mg^{2+}$ rather than $Ca^{2+}$). Moreover, chelators such as BAPTA AM create localized calcium concentration imbalances, and thereby cause secondary movement of calcium in response to the artificially induced reduction in calcium concentration. As such, use of chelators confounds the measurements by blending natural flux and chelator-induced flux, without discrimination.

What is needed, therefore, is a system for tracking the movement of calcium that reduces issues such as those described above, at least in part.

SUMMARY OF THE INVENTION

The present invention overcomes the foregoing problems and other shortcomings, drawbacks, and challenges of tracking movement of calcium within eukaryotic cells. While the invention will be described in connection with certain embodiments, it will be understood that the invention is not limited to these embodiments. To the contrary, this invention includes all alternatives, modifications, and equivalents as may be included within the spirit and scope of the present invention.

The above and other needs are met by a method according to an embodiment of the present invention for tracking calcium flux in a eukaryotic cell, by growing the eukaryotic cell in the presences of a ytterbium salt in solution and spectroscopically measuring ytterbium in the eukaryotic cell.

The disclosed embodiments of the present invention are of benefit for several reasons. Ytterbium ($Yb^{2+}$, but referred to herein as ytterbium or ytterbium ion or cation) is not naturally found in eukaryotic cells, so any detected presence of ytterbium within the cell would be from a non-native source. Ytterbium transports throughout the cell, including into and out of subcellular organelles, in the same manner as calcium. Further, the introduction of ytterbium does not affect the flux of calcium through the cell. In addition, ytterbium is not the same as calcium in terms of their electron configurations, so it may be distinguished from calcium in the cell using methods such as by Raman spectroscopy, electron energy loss spectroscopy, or both.

In accordance with other embodiments of the present invention, a method of tracking calcium flux of a eukaryotic cell includes growing the eukaryotic cell in the presence of a ytterbium salt in solution and applying a stimulus to the eukaryotic cell. The stimulus is configured to induce calcium flux into the eukaryotic cell, throughout the eukaryotic cell, or both. The ytterbium may then be spectroscopically measured in the eukaryotic cell.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Further advantages of the invention are apparent by reference to the detailed description when considered in conjunction with the figures, in which.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Various embodiments of the present invention use ytterbium cation as a surrogate to calcium for intra- and intercellular evaluation. The ytterbium cation has spectral properties that are different than calcium, but may be transported intra- and extracellularly (e.g., similar flux properties) to calcium. Use of embodiments of the present invention might be in biomedical research, such as an assay for tracking calcium movement in live cells in real time without artificially perturbing the local calcium concentrations.

Figure 1:
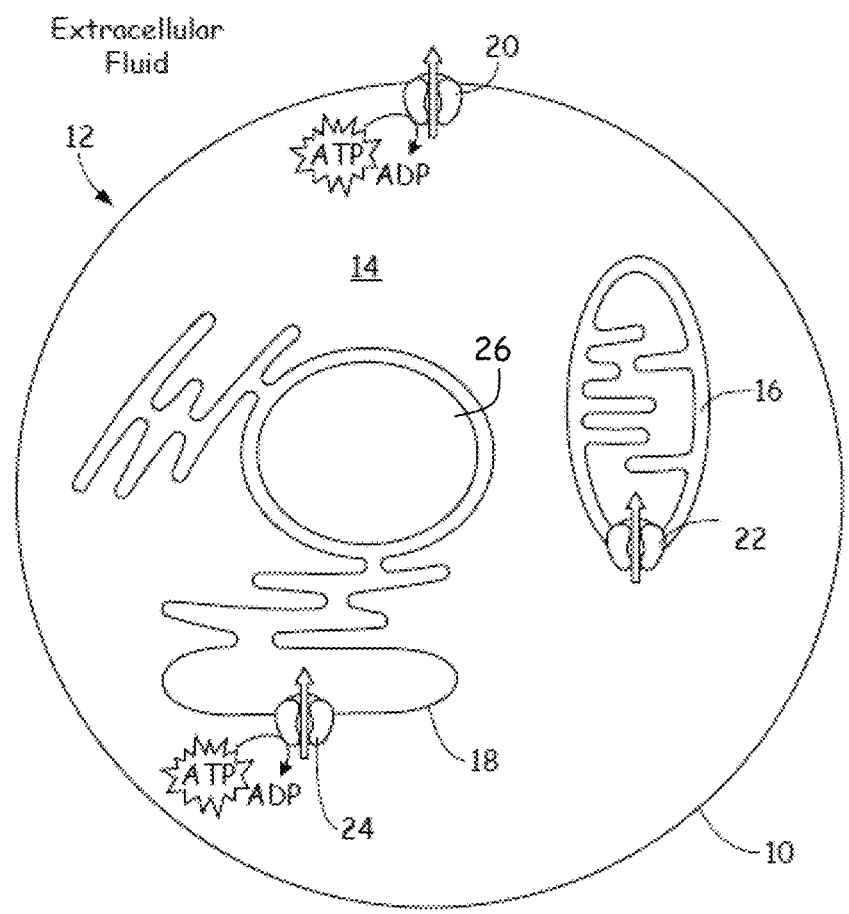
FIG. 1 is a schematic illustration of a eukaryotic cell and calcium transport sites therein.

Ytterbium is a lanthanide, rare earth metal that is physically different from calcium, an alkali-earth metal (see Table 1 below). Therefore, ytterbium may be distinguished from calcium using spectroscopic methods. Because ytterbium has a similar ionic radius and the valence as calcium, ytterbium behaves, physiologically, almost identically to calcium. That is, ytterbium moves in accordance with conventional calcium pathways during physiological signaling and, thus, may be used as a marker of calcium transport. Moreover, because ytterbium is not naturally present in cells, the detected presence of ytterbium in the cytoplasm 14 (FIG. 1) or organelles 16, 18 (FIG. 1) may be inferred as originating from the non-native source.

TABLE 1

| CHARACTERISTIC | CALCIUM | YTTERBIUM (II) |
|---|---|---|
| Atomic number | 20 | 70 |
| Atomic weight (Da) | 40.078 | 173.054 |
| Valence | +2 | +2 |
| Atomic radius (pm) | 194 | 222 |
| +2 Ionic radius (pm) | 114 | 116 |

Ytterbium may be tracked using a variety of atomic spectroscopy techniques, such as electron energy loss spectroscopy (for dead cells) or Raman spectroscopy (for live cells). Because the cells slowly incorporate a relatively small amount of ytterbium, the presence and location of the ytterbium may be tracked, both temporally and spatially, along pathways that are associated with calcium flux.

In one embodiment, the chemical form of the ytterbium used may be ytterbium (II) iodide ($YbI_2$), which dissociates to ytterbium divalent cation and two iodide anions in aqueous solution. In various embodiments, ytterbium may be stabilized using alpha-cyclodextrin, beta-cyclodextrin, or gamma-cyclodextrin in several different ratios. In some embodiments, the ytterbium (II) iodide may be encapsulated with gamma-cyclodextrin ($C_{48}H_{80}O_{40}$) in a 1:1 complex ratio, for example.

Figure 2:
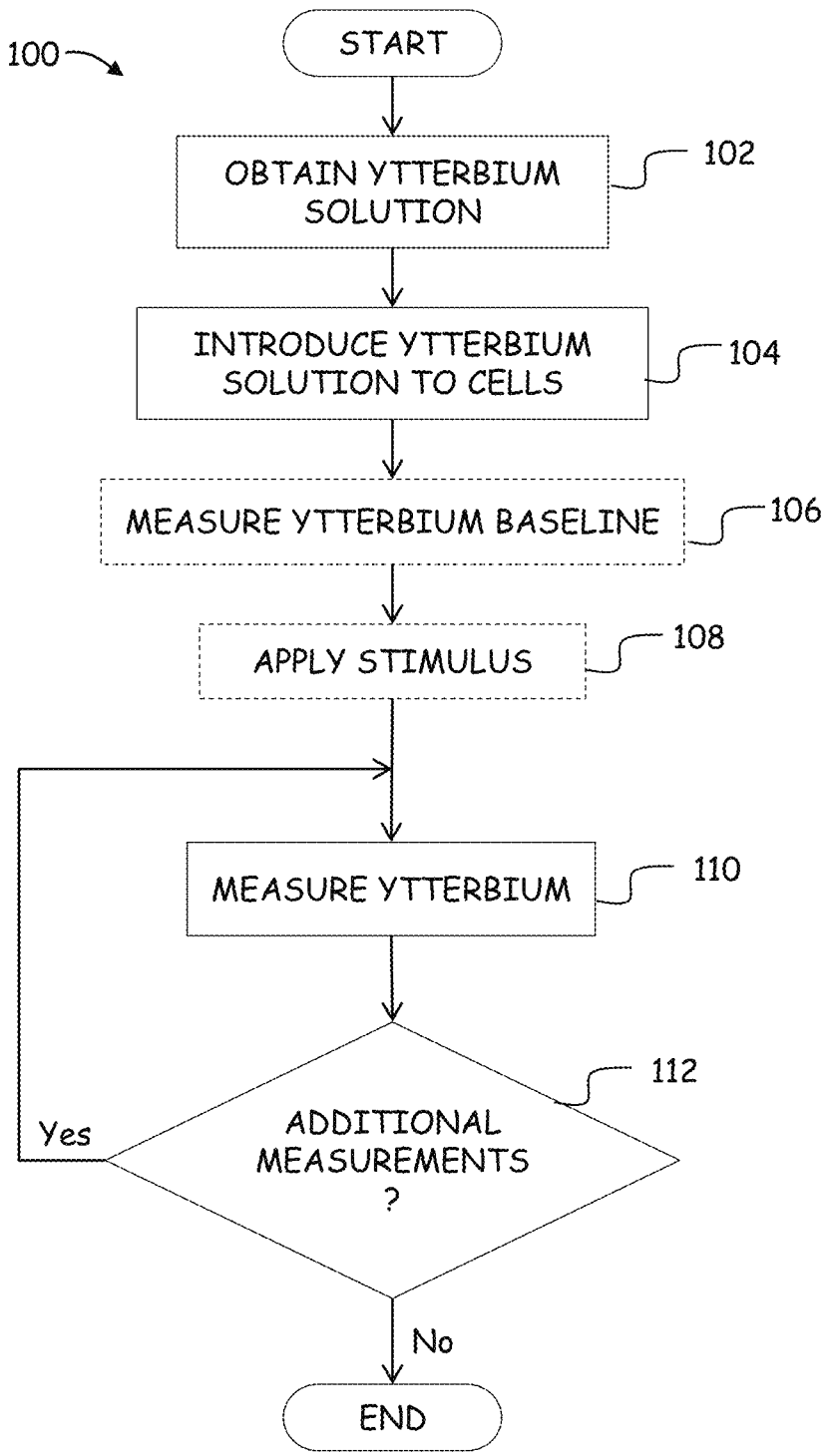
FIG. 2 is a flow chart illustrating a method according to an embodiment of the present invention.

With reference now FIG. 2, there is depicted a method 100 according to an embodiment of the present invention. At the start, a solution comprising a ytterbium salt is prepared (Block 102). The ytterbium solution may include a measured amount of any ytterbium compound easily dissociable in solution to yield divalent ytterbium, such as a ytterbium salt. Suitable ytterbium salts may include, for example, ytterbium (II) iodide, ytterbium (II) chloride, or ytterbium (II) nitrate. In some embodiments, the solution may further include a buffer, an energy or food source, antimicrobials (for reducing bacterial growth), or chelators or encapsulators for encapsulating other chemical agents (such as pharmaceutical drugs). According to some embodiments of the present invention, the solution may be incorporated into a commercially-available agar or another cellular growth medium.

In some embodiments, the ytterbium solution may be available, as from a provided kit. In those embodiments in which ytterbium is provided via a kit, the ytterbium may be premixed with cyclodextrin, such as gamma cyclodextrin, a vessel may be provided and having a mark thereon with the level to which a solvent should be added, instructions for dissolving the ytterbium in a solvent, other instructions and methods as described herein, or combinations thereof.

Once the solution is prepared, the ytterbium solution may be introduced into the cells, such as by irrigation or incubation. Appropriate time periods and temperatures of irrigation or incubation would be known by those having ordinary skill in the art given the benefit of the disclosure provided herein, but may generally range, for example, from about fifteen minutes to about 240 minutes at 37° C., for animal cell lines.

With introduction complete, a baseline measurement of ytterbium in the cells may optionally be acquired (Block 106). Measurement of ytterbium may include one of various imaging modalities that may be configured to discriminate calcium ions from ytterbium ions within the cells. Generally, the baseline measurement may demonstrate calcium concentration throughout the cell cytoplasm and organelles; however, ytterbium may appear only within the cell growth medium or surrounding environment. Alternatively, ytterbium may be observed in those organelles in which ytterbium has been introduced to the cell, such as in the endoplasmic reticulum, the sarcoplasmic reticulum, the mitochondria, or the cytoplasm. Suitable, live cell imaging modalities may include, for example, confocal fluorescence microscopy. In some embodiments, measurements may be acquired observing the spectroscopy effects, such as Raman spectroscopy or electron energy loss spectroscopy ("EELS"), which are described in greater detail below.

As cells grow within the doped medium or agar, ytterbium will be pumped into the cytoplasm alongside calcium uptake. However, for some cell lines, calcium and ytterbium uptake and transfer may not occur without a stimulus. Alternatively, if the cells are pre-exposed to a particular stimulus, then additional stimuli may be required to force calcium and ytterbium flux. As a result, a stimulus may optionally be applied to the cells (Block 108), wherein the stimulus is configured to induce calcium flux down a concentration gradient or via a calcium ion channel, for example. Exemplary stimuli for inducing oxidative stress may include, for example, hydrogen peroxide, sodium cyanide, rotenone, carbonyl cyanide 4-(trifluoromethoxy)phenylhydrazone ("FCCP"), or a combination thereof. For evaluating calcium flux with respect to redox phenomena, co-factors may be introduced as a stimulus. Such cofactors may include any multivalent ion known to promote oxidative stress, including $Fe^{3+}/Fe^{2+}$ (for Fenton-type reactions), $Ce^{3+}/Ce^{4+}$ (for redox fluctuation), or $Pr^{3+}$ (for promoting oxidative stress). Other stimulants may include those configured to promote the formation of NO or for quenching the formation of oxidative radical species. Such stimuli may include exposure to red light, sodium nitrate, or di-nitrosyl iron complex ("DNIC") capped with methyl-protected glucose (pGlu).

With or without the optionally applied stimulus, and after some time, measurements may be acquired for localizing ytterbium within the cells (Block 110). According to one embodiment of the present invention, measurements may be acquired via confocal fluorescence microscopy. When using calcium green dye, samples may be excited at about 507 nm and emission measured at about 529 nm. Alternatively, a label-free Raman approach using Stokes shift from 1670 $cm^{-1}$ to 2845 $cm^-$ may provide a pseudo location of Yb (by using calcium green) or actual location of Yb because calcium ions do not exhibit a Stokes shift at the same reciprocal wavelength. As a result, fluorescence in the cytoplasm or particular organelles using a selective dye or Stokes shifts at aliphatic C—H vibrations (at 2845 $cm^{-1}$) and aliphatic C═C vibrations (at 1670 $cm^{-1}$) may be measured and monitored as an approach that was sensitive to calcium flux. In this manner, changes in calcium, ytterbium, or both, may be observed.

Figure 3A:
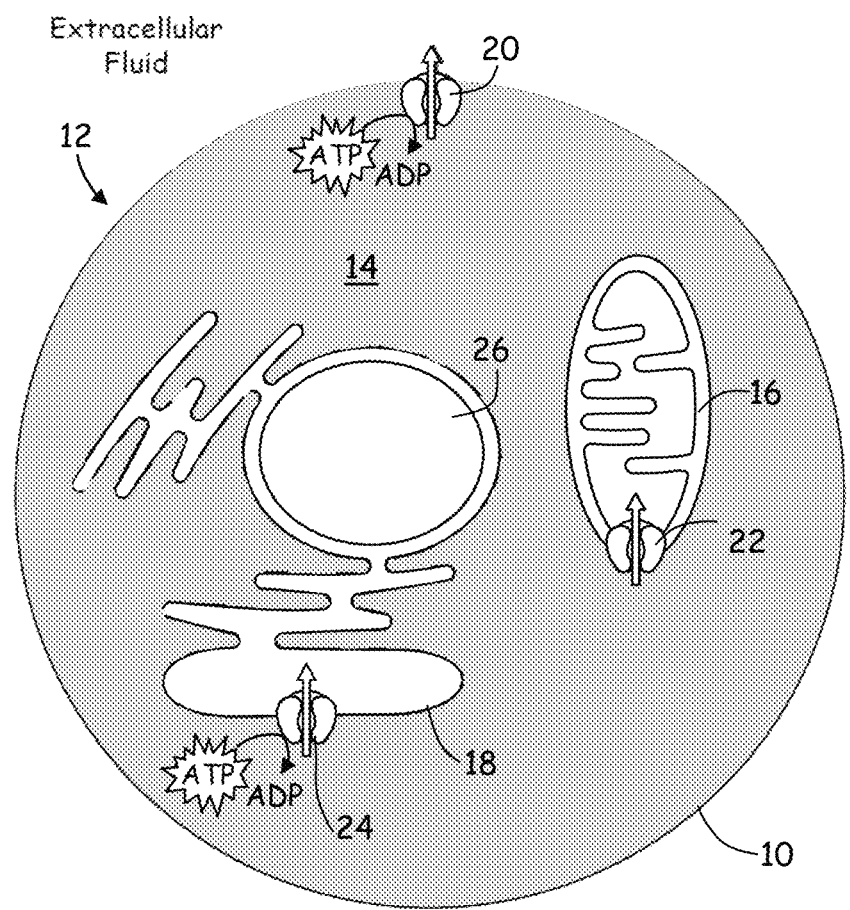
FIGS. 3A and 3B schematic illustrate a presence of ytterbium within the eukaryotic cell.
Figure 3B:
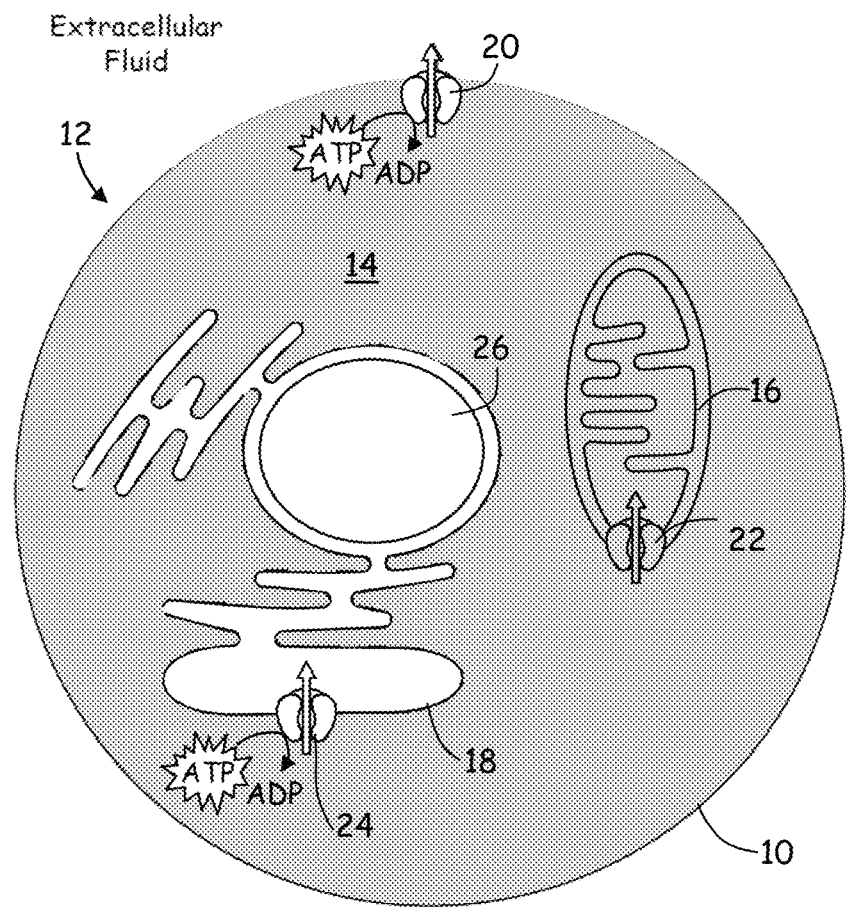

Electron energy loss spectroscopy ("EELS") at 180 eV may also be collected. For example, and as is illustrated in FIG. 3A, the cell 12 has taken up ytterbium into the cytoplasm 14 (illustrated as shading), which may be presumed to be according to calcium uptake channels. If additional measurements are desired ("Yes" branch of Decision Block 112), such as in a temporal investigation of ytterbium movement within the cell 12, then additional measurements may be acquired (returning to Block 110). For example, and as is illustrated in FIG. 3B, ytterbium flux has continued such that fluorescence is detected using a selective dye within the mitochondria 16 (illustrated as shading similar to the cytoplasm 14). When no further measurements are needed or desired ("No" branch of Decision Block 112), then the process may end.

According to other embodiments of the present invention, localization of ytterbium within the cell 14 (FIG. 3A) may be measured by aliphatic C—H vibrations (at 2845 $cm^{-1}$) and aliphatic C═C vibrations (at 1670 $cm^{-1}$) sensitive to calcium flux may be observed at 1080 $cm^{-1}$. A Raman microscopy experiment, described in detail below, may be used.

Any suitable, commercially-available Raman microscope may be used, but generally include an optical microscope, an excitation laser, a spectrometer, and the associated filters, lenses, and detection equipment known by those of ordinary skill in the art. According to one exemplary embodiment, the system includes a 90 argon ion laser operating at 514.5 nm with 150 mW light power focusing to a beam having a diameter of about 0.6 mm to a sample holder. A 300 mm focal length, f/0.6 aspheric lens comprises the collection optics. Data may be collected at a desired repetition rate, such as 1 $cm^{-1}$ at 2 scans per cm such that multiple scans totaling about 1 min integration time per cubic centimeter. According to one specific embodiment, 900 equally wavenumber-spaced samples in each sweep may be zero-padded with an additional 900 samples (900 pixels-per-scan). The combined 1800 samples may be directly Fast Fourier Transformed and converted to log intensity. Axial pixel spacing of 4.4 µm in air corresponds to 3.3 µm in tissue. A standard 6×6 $mm^2$ area, 1400×350 scan volume may be acquired in 1.4 sec. Software data acquisition tools included line scan-rate, scan area, and resolution as adjustment parameters. In automatic mode, the scan rate and data digitization rate may be automatically varied to get the optimal pixel density. Scan times of such exemplary embodiments may range from 0.5 sec to 30 sec and depend on selected scan area and resolution thresholds. The cells or samples may be held in a sample plate having a PBS buffer, pH 7.0. In some embodiments, cell concentration may be diluted, such as to less than about 100 cells/$cm^3$. For purposes of identifying drift, averages of first scans and last scans may be compared in a manner known in the art. For example, the set up may be based on FREUDIGER et al., "Label-free biomedical imaging with high sensitivity by stimulated Raman scattering microscopy," *Science*, Vol. 322 (2008) 1857-1861; A. ZUMBUSCH et al., "Three-dimensional vibrational imaging by coherent Anti-Stokes Raman scattering," *Phys. Rev. Lett.*, Vol. 82 (1999) 4142-4145; H. R. MORRIS et al., "Imaging spectrometers for fluorescence and Raman microscopy: acousto-optic and liquid crystal tunable filters," *Appl. Spectroscopy*, Vol. 48 (1994) 857-866; and K. C. SCHUSTER et al., "Single-cell analysis of bacteria by Raman microscopy: spectral information on the chemical composition of cells and on the heterogeneity in a culture," *J. Microbiol., Methods*, Vol. 42 (2000) 29-38.

The amide I region of Raman spectra (ranging from 1500 $cm^{-1}$ to 1800 $cm^{-1}$) yields fully resolved lipids and does not, typically, exhibit spectral changes indicative of phase changes at high temperatures. Raman spectra within the C—H stretching mode (ranging from 2800 $cm^{-1}$ to 3000 $cm^{-1}$) may be recorded.

Acquired spectra of lipids may be subtracted from acquired spectra of lipid-protein complexes such that the intensity of the lipid ester C═O stretch at 1735 $cm^{-1}$ may be reduced to zero or minimized, and such that the resultant spectrum has a minimum number of inflections near the peak frequency of the sharp lipid, C═C stretching band. Stating the latter another way, the lipid C═C band, which is narrow relative to the amide I band of proteins, may be a sharply inflected curve in the difference spectrum.

Amide I Stokes shifts spectra of calcium or ytterbium may then be analyzed, for example, according to methods described in R. W. WILLIAMS et al, "Protein secondary structure analysis using Raman amide I and amide III spectra," *Methods Enzymol.*, Vol. 130 (1986) 311-331, the disclosure of which is incorporated herein by reference, in its entirety. The secondary structure may be calculated as a sum of fractions of the reference proteins. C—H stretching spectra may be analyzed for the number of linearly independent components using a singular value analysis by the procedure described in incorporated methodology. The methodology provides the advantage of analyzing specific organelles without extensive sample preparation.

Because of the physical and chemical similarities between calcium and ytterbium, the movement of the ytterbium may be equated, qualitatively, to the movement of the calcium. Here, the magnitude of the response (NO fluorescence using a selective dye or change in vibration frequency) may be correlated with no calcium, calcium addition and ytterbium addition, with the response with $Ca^{2+}$ and $Yb^{2+}$ being of about the same magnitude. Qualitative equality may be determined indirectly or directly. According to indirect embodiments of the present invention, a measurement of NO fluorescence may be used. According to direct embodiments of the present invention, edge energies under EELS diagnostics or Stokes shifts under Raman spectroscopy may be used. Thus, by this method 100, as depicted, one is able to effectively watch calcium transport mechanisms in the cells.

Figure 4A:
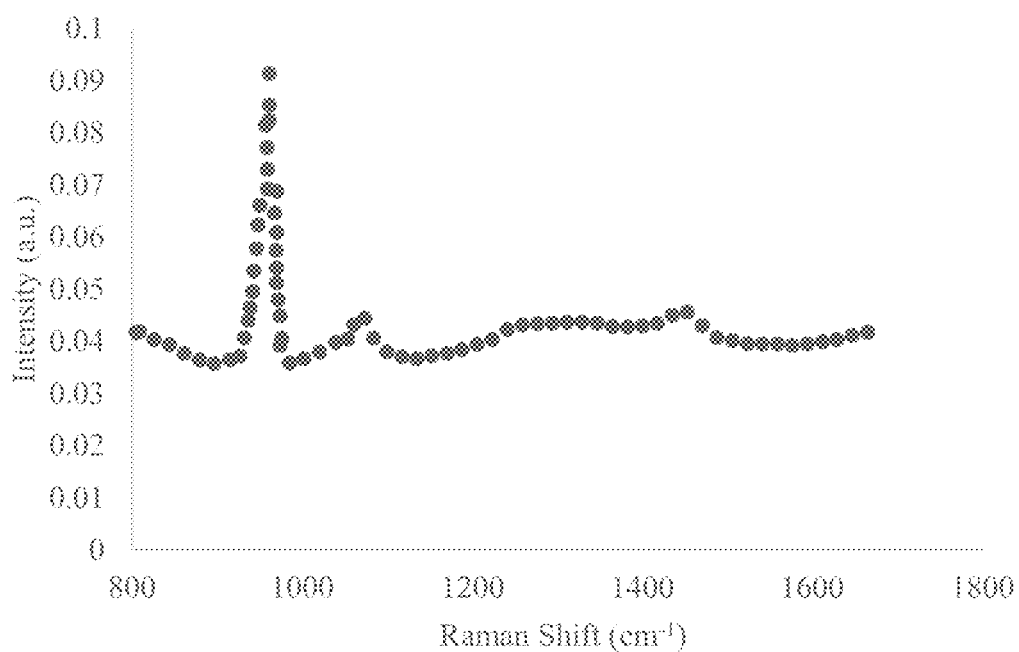
FIGS. 4A and 4B are exemplary Raman spectra showing ytterbium with trace calcium and with calcium, respectively.
Figure 4B:
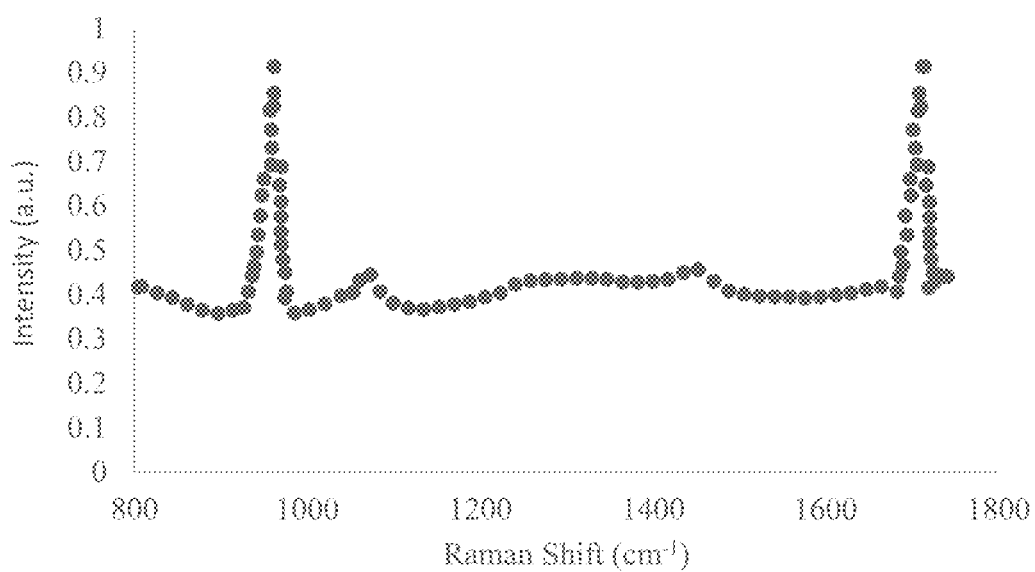

Exemplary Raman spectra showing ytterbium with trace calcium and with calcium are shown in FIGS. 4A and 4B, respectively.

According to other embodiments of the present invention, EELS mapping may be used in alternative to Raman spectroscopy. The EELS instrumentation may include a high-resolution transmission electron microscope ("HRTEM") equipped with an energy dispersive spectroscope ("EDS") analysis. The HRTEM may be operated at 100 keV beam energy and may be set up to provide a very low probe current (about 5 pA) for digital dark-field imaging under minimal electron dose conditions. First and second condenser lenses may also be set to provide a high probe current (about 5 hA) for EELS mapping.

In one exemplary embodiment, EELS spectra may be acquired using a Gataon parallel-detection spectrometer. While integration time may vary, 25 ms for high intensities and a few seconds for weak intensities may be appropriate. To minimize detector dark-current, a temperature of the system photodiode array may be reduced with a thermoelectric cooler. The read-out noise may be optimized by decreasing a number of read-outs so that a maximum number of counts is close to saturation (about $1.6\times10^4$).

Figure 5A:
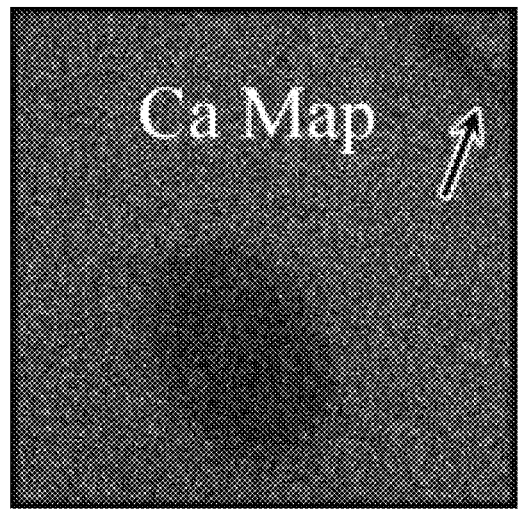
FIGS. 5A and 5B are exemplary EELS images showing calcium without ytterbium and ytterbium without calcium, respectively.
Figure 5B:
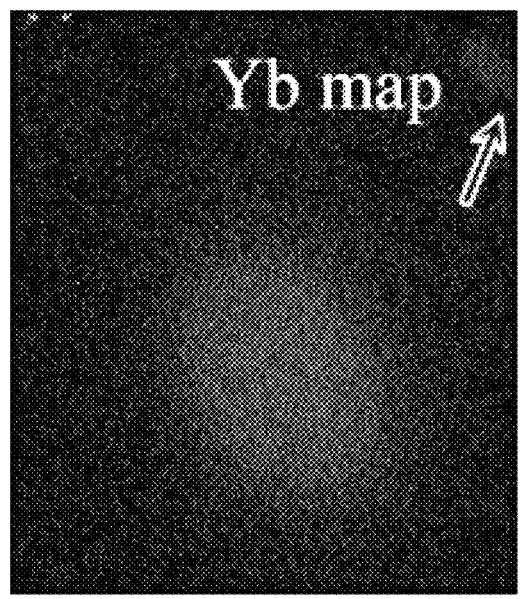

The attainable energy resolution of the spectrometer is approximately 0.4 eV as determined by the intrinsic energy width of the field-emission source. Spectra are transferred to a PC computer from the spectrometer photodiode interface via a direct memory access (DMA). Parallel-EELS mapping of low calcium concentrations in order to allow for high data transfer rates required for spectrum-imaging. In the case of the core-edge spectrum-images from RPE cells, acquisition times were 0.4 s per pixel for a 64×64-pixel map were used. Exemplary EELS imaging demonstrating calcium without ytterbium and ytterbium without calcium and provided in FIGS. 5A and 5B, respectively.

The reference spectra for the Ca $L_{2,3}$-edge from $CaCl_2$ deposited on carbon black (C) is fitted to the $Ca^{2+}$ from the cell samples. The electron loss from 330-420 eV maximal at 350 eV is diagnostic of calcium. Measurement of low calcium concentrations in cryosectioned cells may be accomplished by parallel-EELS mapping. In an analogous fashion, ytterbium can be scanned using Sharp $M_{4,5}$-edges and $Yb_2O_3$ thin film as a reference with a beam energy of 200 kV. The electron loss from 0-380 eV maximal at 180 eV is diagnostic of Yb.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLES

Human retinal pigmented epithelium cells ("RPE"), approximately 120,000 in number, were suspended in phosphate buffered saline ("PBS") and incubated in the dark for 15 min at 37° C. 5 µM 4-amino-5-methylamino-2',7'-dichlorofluorescein diacetate ("DAF-FM DA") was dissolved in dimethyl sulfoxide ("DMSO") and then added to the cells. The cells were then incubated in the dark for an additional 45 min.

Under these growth conditions, RPE cells generate NO, which may be monitored as a function of time or at a fixed time point using fluorescence spectroscopy (excitation and emission wavelengths of DAF-FM DA being 495 nm and 515 nm, respectively).

The grown RPE cells were treated with $CaCl_2$ or YbCD loaded with DAF FM-DA (1 µL, 15 min) in PBS at 37° C., washed, and placed in fresh PBS for imaging. For DAF FM-DA imaging, the cells were exposed to 495 nm light and fluorescence intensity was measured at 515 nm. A median fluorescence intensity of each field of cells was measured using ImageJ. A mean value was then calculated, and a two-tailed student's t-test used to establish statistical significance.

Live cell imaging was performed using a confocal, fluorescent microscope having a 40×, water-immersion objective lens at 37° C., and 5% $CO_2$ environment.

Example 1

Ion Conductivity

To demonstrate selective ion conductivity, ytterbium was compared to other potential surrogates for use in tracking the flux of calcium ions. In that regard, RPE cells were incubated as described above and further included cerium ($Ce^{3+}$, $Ce^{4+}$) and praseodymium ($Pr^{3+}$) as negative controls because cerium ($Ce^{3+}$) and praseodymium ($Pr^{3+}$) have ionic radii that are similar to calcium but exhibit higher charge densities. Iron ($Fe^{3+}$) and lithium ($Li^+$) were also evaluated.

Iron is conventionally used as an oxidizer for determining the propensity of metal ions to create membrane stress through lipid oxidation/peroxidation. Lithium (Li$^+$) was used as a low charge density control, and cerium (Ce$^{4+}$) was used as a high charge density control. The properties of these elements are provided in Table 2, below.

In that regard, RPE cells were suspended in phosphate-buffered saline supplemented with 5 mM magnesium chloride (MgCl$_2$) and 5 mM calcium chloride (CaCl$_2$), the latter being a control against which all values were compared.

TABLE 2

| ELEMENT | ATOMIC NUMBER | VALENCE | IONIC RADIUS |
|---|---|---|---|
| Ytterbium (II) | 70 | 2+ | 116 |
| Cerium (III) | 58 | 3+ | 115 |
| Cerium (IV) | 58 | 4+ | 101 |
| Praseodymium (III) | 59 | 3+ | 113 |
| Iron (III) | 26 | 3+ | 69 |
| Lithium | 3 | 1+ | 90 |

Cells were then imaged and analyzed.

Ionic radius was found to not be the parameter that determines transport through calcium ion channels. The NO control values in RPE without calcium could not be restored with any combination of iron, cerium, or praseodymium, but could be restored back to near control values with ytterbium. Co-supplementation of ytterbium/calcium to RPE cells in a calcium-free PBS buffer resulted in modest NO increases, suggesting that calcium availability in the cytoplasm is not the driving source, but calcium efflux from organelles such as the endoplasmic reticulum to the cytoplasm is the mechanism that drives NO synthesis.

Thus, it appears that, at the cellular level, the cells are able to take up ytterbium into the organelles in the absence of calcium. Since ytterbium does not naturally occur in cells, the results suggest that incorporation of ytterbium in the cellular communication system may be a method to study the role of calcium in cellular communications, stress, aging, and tissue ischemia.

Other formulations considered include: (1) addition of calcium chloride to cells already in the presence of calcium; (2) addition of iron, the catalyst of the Fenton reaction that can cause lipid peroxidation, to decrease NO levels through plasma membrane destabilization; (3) addition of nitrite (NO$_2$) to increase NO levels; and (4) addition of cyanide (CN) to lower NO by blocking mitochondrial respiration. The results demonstrate that ytterbium was able to successfully replace calcium without apparent stress to the cells.

The role of calcium was further investigated by comparing cells without calcium, cells with calcium, and cells with calcium subsequently chelated using N,N'-[1,2-ethanediyl-bis(oxy-2,1-phenylene)]bis[N-[2-[(acetyloxy)methoxy]-2-oxoethyl]]-bis[(acetyloxy)methyl] ester [BAPTA AM]. The corresponding fluorescence levels were lower in cells without calcium and where calcium was chelated using BAPTA AM. To refine the location, co-factors known to interact with the mitochondria (such as FCCP, sodium cyanide, rotenone or oligomycin) were used.

Low calcium concentration in cryosectioned cells was measured by parallel-EELS mapping. Two spectra were collected. The reference spectra for the Ca $L_{2,3}$-edge from CaCl$_2$ deposited on carbon black (C) is fitted to the Ca$^{2+}$ from the cell samples. The electron loss from 330-420 eV maximal at 350 eV is diagnostic of calcium. In an analogous fashion, ytterbium can be scanned using Sharp $M_{4,5}$-edges and Yb$_2$O$_3$ thin film as a reference with a beam energy of 200 kV. The electron loss from 0-380 eV maximal at 180 eV is diagnostic of Yb.

Example 2

Ischemia

When cells are stressed by ischemia, some cells will die due to the lack of oxygen. When oxygen is suddenly reintroduced through reperfusion, further damage is possible through local increases of NO, which is toxic. The magnitude of NO production is determined by an amount of calcium released from the endoplasmic reticulum to the cell cytoplasm. While this mechanism has been studied for decades, the trigger for calcium release is unknown.

Host compounds were prepared by mixing the contents in 1:1 molar ratio of YbI$_2$·γCD (αCD or βCD could also have alternatively been used) and ytterbium diiodide with constant stirring in a round bottom flask. When the ytterbium diiodide was added there was an evolution of hydrogen gas. The mixture was heated in a closed beaker to sublimate the iodine on the top and walls of the container. This was repeated two to three times to remove most of the iodine as a sublimate and so that very little iodine remained, which produced about a 73% by mass yield of a yellow-colored crystalline substance.

For some tests, the temperature ranged from about 50° C. to about 70° C. For some tests, water was used as the solvent. Both the inclusion of cyclodextrin and heating of the solution increased the solubility of the ytterbium (II) diiodide. Heating also facilitates sublimation of iodine. The results are summarized in Table 3, below. Agents tested include: CN, [Ca-PBS], Li$^+$, Mg$^{2+}$, Fe$^{3+}$, Ce$^{3+}$, and Pr$^{3+}$.

NO fluorescence was measured using a NO-specific probe in the form of 4-amino-5-methylamino-2',7'-Difluorofluorescein Diacetate (DAF-FM DA). RPE cells were suspended in phosphate buffered saline with a final DAF-FM DA concentration of 5 μM along with other NO-inducing and NO-inhibiting ions. Such ions included: nitrite and metal salts of iron (III), praseodymium (III), equal-volume calcium ion and praseodymium (II), cerium (III), sodium nitroprusside (SNP), dithranol, sodium cyanide, dinitrosyl iron complex (DNIC) capped with methyl-protected glucose (pGlu), and nitrite. The concentration, unless otherwise stated, was 300 parts-per-million (ppm). Total well volume was 175 μL composed as follows: 150 μL cells+25 μL PBS±Ca, 150 μL cells+20 μL PBS±Ca+5 μL chemical agent, or 150 μL cells+15 μL PBS±Ca+10 μL chemical agent.

Sodium nitroprusside (SNP) concentration varied widely over time due to binding and release of CN, which resulted in increases and decreases of measured NO. The total difference (between the lowest value and the highest value) is shown. Generally, the value increased with time, became constant, and finally, near the end, decreased. The effect of the rapid release of Ca$^{2+}$ was a transient decrease followed by a general increase of NO. The transient decrease may be a down-regulation of nitric oxide synthase which is, in part, regulated by basal levels of NO. With time, the measured values increased to approximately 125% of control (not summarized in Table 3), although the final NO fluorescence was dependent upon the volume of agent used and its stock concentration.

TABLE 3

| COMBINATIONS | [(E − C)/C] × 100 (N = 3, A.U. %) | ±STD DEV OF FLUORESCENCE (N = 3, A.U. %) | P < 0.001 | DESCRIPTION OF CONTROL |
|---|---|---|---|---|
| WT 5 mM $Ca^{2+}$ + $Mg^{2+}$ | 0% | 4% | N | Control, arbitrarily set at 0% + 8 mM pyruvate |
| WT + $Fe^{3+}$ | −93% | 1% | Y | Examine role of Fenton-Type oxidation |
| WT + $Pr^{3+}$ | −91% | 11% | N | Slightly smaller ionic radii to $Ca^{2+}$ used as negative control |
| WT + $Ca^{2+}$ + $Pr^{3+}$ | −88% | 5% | N | To examine whether there is competition between $Ca^{2+}$ & $Pr^{3+}$ |
| WT + $Ce^{3+}$ | −96% | 10% | Y | Ionic radii slightly larger than $Ca^{2+}$ used as negative control |
| WT + Nitroprusside ($C_5FeN_6O$, SNP, 100 μM) | −78% | 106% | N | Effect of ultraslow release of NO on calcium use on mitochondria |
| WT + Dithranol ($C_{14}H_{10}O_3$, DIT, 100 μM) | −69% | ~15% | N | Effect of $Ca^{2+}$ use in reducing environment |
| WT + Cyanide (NaCN 100 μM) | −52% | 9% | N | Effect of binding of CN to complex IV in mitochondria |
| WT + methyl-glucose dinitrosyliron complex (Fe-DNIC 1000 ppm) | −7% | 0.01% | N | Effect of rapid release in cytoplasm on calcium use |
| WT + Nitrite ($NaNO_2$ 100 μM) | 2% | 6% | N | Effect of electron donating agent on calcium use in mitochondria |
| WT + $Yb^{2+}$ | −0.02% | 5% | N | Positive control for calcium (100 μM) |
| WT − $Ca^{2+}$ | −98% | 8% | Y | Effect of absence on $Ca^{2+}$ |
| WT − $Ca^{2+}$ plus agent | −108% | 11% | Y | Cells were unresponsive to chemical stimuli in the absence of Ca2+ and NO levels were near identical across the board, i.e., were 1-fold lower than controls | where WT means whole, wild-type RPE cells.

Table 3, above, predominately addresses the control systems. Table 4, below, specifically addresses the role of ytterbium. Data from RPE-Ca are not shown, since all measured values were similar, except for Fe-DNIC and sodium nitroprusside, which were higher than control by 3% to 6%.

All of the controls listed above in Table 3 demonstrated the feasibility of the NO bioassay to evaluate changes in calcium. From Table 3 it appears that the calcium-ion channels are not triggered by effective ionic radii since the addition of praseodymium yields a slight (102% to 80%, modal 91%) decrease of NO (as low DAF-FM DA fluorescence) over cells not incubated with additional calcium. The corresponding DAF-FM DA fluorescence for RPE cells in the calcium-supplemented, buffered saline control was normalized to 0% change. The addition of praseodymium and calcium in equal amounts decreased the percent change in fluorescence incrementally, but the amount never returned to the levels of the controls (set at 0%). A similar trend was observed with the addition of iron or cesium. These lower NO values could be attributed to lipid peroxidation catalysis via Fenton-like oxidation by iron, cerium, and praseodymium. To confirm that RPE cells underwent plasma membrane disassembly, Raman images of RPE cells exposed to cesium were obtained through a commercial vendor.

Further analyses of the lipid membrane using time-lapse photography with $Ce^{3+}$ in RPE WT cells by Raman microscopy (looking at the lipid vibration frequency at 1670 $cm^{-1}$) may suggest disassembly. Correlation between the fluorescence data using DAF-FM DA with cesium and ytterbium, Raman spectroscopy of cerium, and extrapolation of what is then anticipated for ytterbium by Raman spectroscopy suggests that ytterbium would not cause oxidative stress in the cells (like cesium), but would biochemically behave more like calcium.

Since highly charged ions such as $Pr^{3+}$, $Ce^{3+}$, and iron are known to induce stress, it appears that the degree of cellular stress and NO basal levels are loosely related. This relationship is also captured using Raman imaging. The normal cells do not show signs of stress, since the plasma membrane is intact. This suggests that the cellular load of calcium may be visualized indirectly through measurement of NO. Here mM levels of calcium yield high NO fluorescence through DAF-FM DA, whereas negligible calcium (using calcium-free phosphate buffered saline, −98%) yields low NO fluorescence. Although a generalization, RPE WT cells in calcium-free PBS buffer did not produce any NO regardless of treatment group. The average response was between −98% and 108% relative to the normalized value of 0%. The calcium-lipid vibration stretch frequency (2845 $cm^{-1}$ for aliphatic C—H vibrations and 1670 $cm^{-1}$ for aliphatic C=C vibrations) may also be monitored by Raman, as would the ytterbium-lipid frequency. Since the experiment to control ratios of calcium and ytterbium are similar (as shown below in Table 4), the data suggest that ytterbium does not exert the same oxidative stress as the other transition metal ions The addition of sodium cyanide (Table 3) causes NO levels to decrease. This likely occurs because cyanide is a reversible inhibitor of complex IV in the mitochondria, which accomplishes the two-electron reduction of $O_2$ to $H_2O$ and the reduction of nitrite to NO. Calcium ions in mitochondria are required for this activity because, in calcium-free media, the addition of cyanide does not lower NO levels, i.e., [WC−Ca]No intensity is about the same as [WC−CA+CN]No. A drop in NO fluorescence is only observed when calcium is present during the addition of CN ([WC+Ca]$_{NO}$>>[WC+Ca+CN]$_{NO}$). Since cyanide is known to target the mitochondria, it may be inferred that calcium release from the mitochondrial stores to the cytoplasm results in fluctuations in measured NO.

Dithranol ($C_{14}H_{10}O_3$) is a mild reducing agent, which reduces the phospholipids in the plasma membrane. We anticipated that NO levels would increase as a relative percent of controls and, as demonstrated in Table 3, this was confirmed.

SNP [$Na_2[Fe(CN)_5NO]Na_2[Fe(CN)_5+NO$] is a source of NO that releases NO slowly. Time course measurements of NO fluorescence would suggest that the relative percent change would be positive and this was confirmed experimentally. Nitric oxide release using a dinitrosyl iron complex (DNIC) also demonstrated an increase in measured NO, although this was less than SNP. Historically, SNP ingestion was treated in a similar fashion to classic cyanide poisoning, suggesting that both sodium cyanide and cyanide from SNP bind to complex IV (ferriheme $a_3$) of the mitochondria.

Mitochondrial metabolic activity could be examined by the MTT assay (reduction of 3-[4,5 dimethylthiazol-2-yl]-2,5-diphenyltetrazolium bromide); however in our assay, with results as summarized in Table 3, percent NO levels fluctuate upwards upon incubation with dithranol, and we infer any NO changes are in part a result of calcium changes in the mitochondria. This was inferred by comparing the NO fluorescence between cells in PBS buffer versus cells in calcium-free PBS buffer without and with controls such as sodium cyanide, dithranol, and sodium nitroprusside. This was confirmed by addition of sodium nitrite ($NaNO_2$) which is reduced to NO enzymatically by nitrite reductase or $Fe^{2+} \rightarrow Fe^{3+}$ by the heme in complex IV.

The $Fe^{3+}$, $Pr^{3+}$, and $Ce^{3+}$ ions served as negative controls and, upon addition of these agents, NO levels dropped by varying degrees. Sodium nitrite, SNP, and Fe-DNIC served as "biological" NO sources and DAF-FM DA fluorescence increased relative to control (RPE cells in PBS supplemented with $Ca^{2+}$ and $Mg^{2+}$) in their presence.

The NO-releasing agent based on dinitrosyl iron complex [DNIC] coordinated to a protected glucose molecule [pGlu DNIC] was synthesized specifically for this project. The DNIC was used to arbitrarily increase NO levels; one mole of DNIC releases two moles of NO as per stoichiometry. As anticipated, DAF-FMDA fluorescence increased upon addition of DNIC. Since the DNIC did not have a mitochondrial target protein, it is unlikely that the DNIC translocated to the mitochondria; however, the DNIC was water soluble and likely diffused NO into the cytosol, where it may be translocated to the mitochondria. Regardless of the precise location of DNIC, NO levels increased immediately upon addition of DNIC and were consistent with the calcium transduction pathway. DNIC added to cells with calcium generated more NO than cells without calcium, suggesting that the measured NO was not attributable to the DNIC alone, and the biological NO was generated by NO synthase and/or complex IV.

The relationship between external addition of NO and calcium load is not straightforward, since both calcium ions and NO are used as chemical messengers; however, both species appear to protect cells against oxidative stress and apoptosis. Therefore, to understand the biochemical pathways, one can monitor changes in the levels of calcium ion and NO. NO can be monitored using DAF-FM DA, and we propose that calcium can be monitored indirectly through imaging of ytterbium in cells that have been infused with ytterbium ions.

The data from Table 3 validates the bioassay method as being responsive to NO changes and summarized by the experimental workflow.

Since NO is sensitive to cellular stress and calcium levels, in the first set of experiments summarized in Table 3, calcium levels were kept near saturation levels (about 5 mM) since cells were in PBS that was supplemented with $Mg^{2+}$ and calcium, labeled as PBS±Ca system. A similar experiment was conducted with RPE cells in calcium-free PBS.

The trends are shown bracketed into three general groupings, R, S, and T in Table 4, below.

TABLE 4

| COMBINATIONS | [(E − C)/C] × 100 (N = 6, A.U. %) | ±STD DEV OF FLUORESCENCE (N = 6, A.U. %) | GP | DESCRIPTION OF CONTROL |
|---|---|---|---|---|
| WT (5 mM $Ca^{2+}$ and $Mg^{2+}$) | 0.00% | 2% | R | Control, arbitrarily set at 0%. Also contain 8 mM pyruvate |
| WT + 5 µL $Ca^{2+}$ | 3% | 5% | R | Additional $Ca^{2+}$ does not significantly change NO levels |
| WT + 5 µL $Yb^{2+}$ | 3% | 6% | R | Used as positive control. |
| WT + 5 µL $Yb^{2+}$ + 5 µL $Ca^{2+}$ | 32% | 6% | S | Combinatorial use lowers NO values |
| WT + 10 µL $Yb^{2+}$ | 5% | 3% | S | Increase in volume does not significantly increase NO levels |
| WT + 25 µL $Ca^{2+}$ | 15% | 27% | S | A five-fold increase does not increase NO levels significantly |
| WT + BAPTA | 11% | 4% | T | Used as negative control |
| WT + BAPTA + $Li^+$ | 4% | 4% | T | Used as negative charge control |
| WT + BAPTA + $Ca^{2+}$ | 19% | 4% | T | Used as negative buffer capacity control |
| WT + BAPTA + $Yb^{2+}$ | 14% | 4% | T | Used as positive buffer capacity control | where WT means whole, wild-type RPE cells.

Table 4 shows ratios of DAF-FM DA fluorescence as an indicator of NO in RPE cells with various other NO-inducing (positive controls) and NO-inhibiting (negative controls) ions. Approximately 120,000 cells/well were used. Metal salts of calcium, ytterbium, equi-volume calcium and ytterbium with calcium- chelator agent BAPTA alone or with lithium, calcium, or ytterbium ions. The concentration, unless otherwise stated, was 300 parts-per-million, (ppm). Total well volume was 175 µL and included: 150 µL cells+25 µL PBS±Ca or 150 µL cells+20 µL PBS±Ca+5 µL chemical agent or 150 µL cells+15 µL PBS±Ca+10 µL chemical agent. All other conditions were kept the same for all systems and the DAF-FM DA fluorescence was measured 30 minutes after the addition of ytterbium or calcium or combinations thereof, with and without calcium chelator BAPTA AM.

Supplementation of the buffer with suspended cells that already had 5 mM $Ca^{2+}$ with an additional 5 µL of 5 mM $Ca^{2+}$ resulted in a slight decrease in NO. The difference between RPE and RPE+$Ca^{2+}$ was not statistically significant. Addition of 5 µL of $Yb^{2+}$ to Ca-free RPE cells resulted in an increase in NO equal to, or greater than, control demonstrating that ytterbium does not catalyze Fenton-type reactions, is not cytotoxic and chemically yields NO levels similar to that given by calcium supplements. Since calcium in PBS does not translocate to the mitochondria, but to the cytosol, the NO levels appear to be sensitive to the ratio of calcium between the organelle (the mitochondria) and the cytosol, rather than an absolute trigger concentration for signal transduction.

Co-addition of equal volumes of calcium and ytterbium [2.5 mM: 50 µM] resulted in a drop in NO levels. This drop is not statistically significant, due to the large standard deviation. If NO production is dependent upon calcium efflux, presumably endoplasmic reticulum stores to the cytoplasm through calcium channels, then NO fluorescence would be sensitive to calcium in both the cytoplasm and endoplasmic reticulum. Ytterbium "off rate" is not related to the effective ionic radius, but to the degree of covalency and coordination within the calcium channel entrance. Since ytterbium is slower at exiting the calcium channel than other rare-earth transition metals, its hydration shell may be smaller or its degree of interaction within the channel greater.

The foregoing description of embodiments of this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of tracking calcium flux of a eukaryotic cell, the method comprising:
    growing the eukaryotic cell in the presence of a ytterbium salt in solution;
    spectroscopically measuring a location of ytterbium ions in the eukaryotic cell; and
    correlating the measured location of the ytterbium ions to a location of calcium ions,
    wherein the ytterbium ions are transported intra- and extracellularly with calcium ions.

2. The method of claim 1, further comprising:
    applying a stimulus to the eukaryotic cell, the stimulus configured to induce movement of calcium ions and ytterbium ions into the eukaryotic cell.

3. The method of claim 1, wherein the applied stimulus induces oxidative stress.

4. The method of claim 3, wherein the applied stimulus includes applying hydrogen peroxide, sodium cyanide, rotenone, carbonyl cyanide 4-(trifluoromethoxy)phenylhydrazone ("FCCP"), or a combination thereof.

5. The method of claim 1, wherein the applied stimulus induces a redox phenomena.

6. The method of claim 5, wherein the applied stimulus includes applying a cofactor selected from the group consisting of $Fe^{3+}/Fe^{2+}$, $Ce^{3+}/Ce^{4+}$, or $Pr^{3+}$.

7. The method of claim 1, wherein the applied stimulus promotes formation of nitric oxide.

8. The method of claim 7, wherein the applied stimulus includes applying light, sodium nitrate, or di-nitrosyl iron complex capped with methyl-protected glucose.

9. The method of claim 8, wherein a wavelength of the applied light ranges from about 495 nm to about 515 nm.

10. The method of claim 1, wherein spectroscopically measuring the location of ytterbium ions further comprises:
    observing fluorescence of calcium green within the range of 506 nm to 530 nm, observing Raman vibration frequencies between 1670 $cm^{-1}$ to 2845 $cm^{-1}$, observing electron energy loss at about 1800 eV, or a combination thereof.

11. The method of claim 1, wherein growing the eukaryotic cell in the presence of a ytterbium salt in solution comprises:
    preparing a ytterbium-doped growth medium; and
    growing the eukaryotic cell in the ytterbium-doped growth medium.

12. A method of tracking calcium ion flux of a eukaryotic cell, the method comprising:
    growing the eukaryotic cell in the presence of a ytterbium salt;
    applying a stimulus to the eukaryotic cell, the stimulus configured to induce movement of calcium ions and ytterbium ions into the eukaryotic cell, throughout the eukaryotic cell, or both;
    spectroscopically measuring a location of ytterbium ions in the eukaryotic cell; and
    correlating the measured location of the ytterbium ions to a location of calcium ions,
    wherein the ytterbium ions are transported intra- and extracellularly with calcium ions.

13. The method of claim 12, wherein the applied stimulus induces oxidative stress, a redox phenomena, promotes formation of nitric oxide, or a combination thereof.

14. The method of claim 12, wherein the applied stimulus includes applying hydrogen peroxide, sodium cyanide, rotenone, carbonyl cyanide 4-(trifluoromethoxy)phenylhydrazone ("FCCP"), or a combination thereof.

15. The method of claim 12, wherein the applied stimulus includes applying a cofactor selected from the group consisting of $Fe^{3+}/Fe^{2+}$, $Ce^{3+}/Ce^{4+}$, or $Pr^{3+}$.

16. The method of claim 12, wherein the applied stimulus includes applying light, sodium nitrate, or di-nitrosyl iron complex capped with methyl-protected glucose.

17. The method of claim 12, wherein spectroscopically measuring the location of ytterbium ions further comprises:
    observing fluorescence of calcium green within the range of 506 nm to 530 nm, observing Raman vibration frequencies between 1670 $cm^{-1}$ to 2845 $cm^{-1}$, observing electron energy loss at about 1800 eV, or a combination thereof.

* * * * *